(12) United States Patent
Ullrich et al.

(10) Patent No.: US 9,719,774 B2
(45) Date of Patent: Aug. 1, 2017

(54) METHOD FOR DETECTING CRACKS IN AN AIRCRAFT OR GAS TURBINE COMPONENT

(75) Inventors: Thiemo Ullrich, Hamburg (DE); Michael Ernst, Pinneberg (DE)

(73) Assignee: LUFTHANSA TECHNIK AG, Hamburg (DE)

(*) Notice: Subject to any disclaimer, the term of this patent is extended or adjusted under 35 U.S.C. 154(b) by 704 days.

(21) Appl. No.: 13/479,316

(22) Filed: May 24, 2012

(65) Prior Publication Data
US 2012/0297600 A1    Nov. 29, 2012

Related U.S. Application Data

(60) Provisional application No. 61/512,486, filed on Jul. 28, 2011.

(30) Foreign Application Priority Data

May 24, 2011   (DE) .......................... 10 2011 103 003

(51) Int. Cl.
| | |
|---|---|
| *B23P 6/00* | (2006.01) |
| *G01B 9/02* | (2006.01) |
| *G01B 11/24* | (2006.01) |
| *G01N 21/95* | (2006.01) |

(52) U.S. Cl.
CPC ............ *G01B 9/0209* (2013.01); *B23P 6/002* (2013.01); *G01B 11/2441* (2013.01); *G01N 21/9515* (2013.01); *B23P 2700/01* (2013.01); *Y10T 29/49869* (2015.01)

(58) Field of Classification Search
CPC ...... B23P 6/002; B23P 2700/01; F01D 5/005; G01B 11/2441; G01M 21/9515; Y10T 29/49318; Y10T 29/49769; G05B 19/4202

USPC .............................. 29/889.1, 402.01, 402.09
See application file for complete search history.

(56) References Cited

U.S. PATENT DOCUMENTS

| | | | | |
|---|---|---|---|---|
| 781,385 | A | * | 1/1905 | Narcus ..................... H04R 1/12 |
| | | | | 379/452 |
| 4,340,306 | A | * | 7/1982 | Balasubramanian ......... 356/513 |
| 5,257,088 | A | | 10/1993 | Tyson, II et al. |
| 5,430,935 | A | * | 7/1995 | Yaworsky et al. ........... 29/889.1 |
| 5,563,417 | A | | 10/1996 | Gillard et al. |
| 5,905,260 | A | | 5/1999 | Sage et al. |
| 5,913,555 | A | * | 6/1999 | Richter et al. ............... 29/889.1 |

(Continued)

FOREIGN PATENT DOCUMENTS

| | | |
|---|---|---|
| DE | 19708582 A1 | 9/1998 |
| DE | 19924607 A1 | 11/2000 |

(Continued)

OTHER PUBLICATIONS

KORAD3D Product web page on http://www.3d-shape.com, Jun. 16, 2004, http://http://web.archive.org/web/20040616122457/http://www.3d-shape.com/produkte/korad_e.php.

*Primary Examiner* — Jermie Cozart
(74) *Attorney, Agent, or Firm* — Leydig, Voit & Mayer, Ltd.

(57) ABSTRACT

A method for detecting cracks in an aircraft or gas turbine component includes ascertaining geometric data about the component using an optical measurement method, analyzing the geometric data, using an electronic evaluation device, so as to automatically recognize and/or classify at least one of cracks and other damage and storing a position of the at least one of cracks and other damage.

10 Claims, 1 Drawing Sheet

(56) References Cited

U.S. PATENT DOCUMENTS

| | | | |
|---|---|---|---|
| 6,028,670 A * | 2/2000 | Deck | 356/497 |
| 6,195,168 B1 * | 2/2001 | De Lega et al. | 356/497 |
| 6,195,891 B1 | 3/2001 | Chen et al. | |
| 6,597,460 B2 * | 7/2003 | Groot | G01B 11/30 356/497 |
| 7,017,421 B2 | 3/2006 | Kehlenbach | |
| 8,247,733 B2 * | 8/2012 | Zhu | B23K 26/03 219/121.63 |
| 8,269,980 B1 * | 9/2012 | Szwaykowski | G01B 11/2441 356/504 |
| 2004/0262277 A1 * | 12/2004 | Mika et al. | 219/121.85 |
| 2007/0039175 A1 * | 2/2007 | Rucker et al. | 29/889.1 |
| 2007/0090309 A1 * | 4/2007 | Hu et al. | 250/559.45 |
| 2007/0157447 A1 * | 7/2007 | Prevey | 29/402.01 |
| 2011/0043822 A1 * | 2/2011 | Hamano et al. | 356/515 |
| 2012/0297600 A1 | 11/2012 | Ullrich et al. | |
| 2013/0188059 A1 * | 7/2013 | Georgeson et al. | 348/169 |

FOREIGN PATENT DOCUMENTS

| | | | | |
|---|---|---|---|---|
| DE | 10010019 C1 | 8/2001 | | |
| DE | 69631156 T2 | 11/2004 | | |
| EP | 1357375 A2 | 10/2003 | | |
| EP | 1422380 A2 * | 5/2004 | | F01D 5/00 |
| WO | WO 2010130962 A1 * | 11/2010 | | G01B 11/24 |
| WO | WO 2012159721 A1 | 11/2012 | | |

\* cited by examiner

METHOD FOR DETECTING CRACKS IN AN AIRCRAFT OR GAS TURBINE COMPONENT

CROSS REFERENCE TO RELATED APPLICATIONS

This application claims priority to both German Patent Application No. 10 2011 103 003.8, filed May 24, 2011, and U.S. Patent Application No. 61/512,486, filed Jul. 28, 2011, which are hereby incorporated by reference herein in their entirety.

FIELD

The present invention relates to a method and a device for detecting cracks in an aircraft or gas turbine component.

BACKGROUND

Aircraft components are subject to high stresses in operation. This can lead to a faulty crack formation, not only in components made of composite materials, such as structural or metallic components, for example landing-gear components, but also in aircraft engine components, in particular. Similar damage patterns are also evident in other gas turbines, such as in stationary gas turbines. The combustion chamber components in gas turbines are highly susceptible to cracking.

Cracks are local material separations within a structure or within a component. Normally, crack initiation is a local event in the microstructure of a surface that is typically caused by lattice defects in the microstructure or by cyclical operational loads. As a rule, cracks propagate orthogonally to the acting normal stress. This propagation is characterized as a normal stress-controlled process.

In the case of combustion chamber components, cracks form due to high thermal and mechanical loads. On the one hand, the prevailing high temperatures cause the cracks to form; on the other hand, the vibrations transmitted to the combustion chamber from the upstream and downstream modules, the high-pressure compressor and the high-pressure turbine promote crack growth and formation. Moreover, short-term thermal material stresses during gas turbine start-up and, as the case may be, during the starting phase of aircraft operation, encourage crack initiation. Solid particles, such as sand and dust, which are drawn into the gas turbine, are likewise highly conducive to crack initiation in the combustion chamber components. Moreover, during the gas turbine's operating phase, sustained thermal stresses induce a change in the geometric shape of the combustion chamber components.

The main problem associated with maintaining and servicing aircraft and/or gas turbine components, particularly with maintaining and servicing the combustion chamber, is detecting the cracks that form and the geometric variations that arise during operation, and repairing the components through appropriate measures. This is often difficult to accomplish due to the unique characteristics of the particular cracks or damage.

Known methods for detecting cracks include a number of non-destructive testing procedures. Current methods include the dye penetration method, ultrasonic testing, eddy-current testing, X-ray testing and magnetic powder testing, for example.

In the majority of components, in particular in aircraft engine components, such as combustion chamber components, for example, the dye penetration method is used to test for cracks.

The dye penetration method usually encompasses at least the following five steps:
1. precleaning and drying the test specimen to remove accumulated dirt from between the crack flanks;
2. applying what is generally referred to as the penetrant (penetrating oil having fluorescent pigments) that penetrates into the cracks;
3. intermediate drying (removing the excess penetrant) and drying;
4. applying what is generally referred to as the developer (chalk-based powder) to make the cracks visible;
5. manual analysis of the indications under ultraviolet light by trained personnel. The indications (for example, cracks) are marked on the test specimen.

Following the dye penetration test, the test specimen undergoes a visual control. A manual inspection is performed to check whether the indications are actually cracks and whether the marked crack indications are within the permissible tolerance. The tolerances for the component in question are specified in the technical maintenance and service documentation.

Following the visual control, geometric measurements of the test specimen are likewise taken manually. The dimensions and measuring positions to be checked are defined in the technical service documentation. Trained specialists measure the test specimen using measuring implements, such as a special measuring tape, for example, and the exact geometric data are subsequently documented.

The dye penetration method actually used for the components is a manual method that is quite time-consuming. Due to its many process steps, the dye penetration test substantially influences the process and processing time needed for component maintenance. Moreover, test reproducibility is not or at least not fully given as the indications are analyzed manually. The test quality is influenced by the human factor. Moreover, dye penetration is a chemical and energy-intensive test procedure. Therefore, it has an environmental impact.

SUMMARY

Therefore, an aspect of the present invention is to provide an improved method and a corresponding device for detecting cracks in an aircraft component and/or gas turbine component.

In an embodiment, the present invention provides a method for detecting cracks in an aircraft or gas turbine component. The method includes ascertaining geometric data about the component using an optical measurement method, analyzing the geometric data, using an electronic evaluation device, so as to automatically recognize and/or classify at least one of cracks and other damage and storing a position of the at least one of cracks and other damage

BRIEF DESCRIPTION OF THE DRAWINGS

The present invention is clarified in greater detail in the following on the basis of preferred specific embodiments with reference to the enclosed figures, which show.

DETAILED DESCRIPTION

Figure 1:
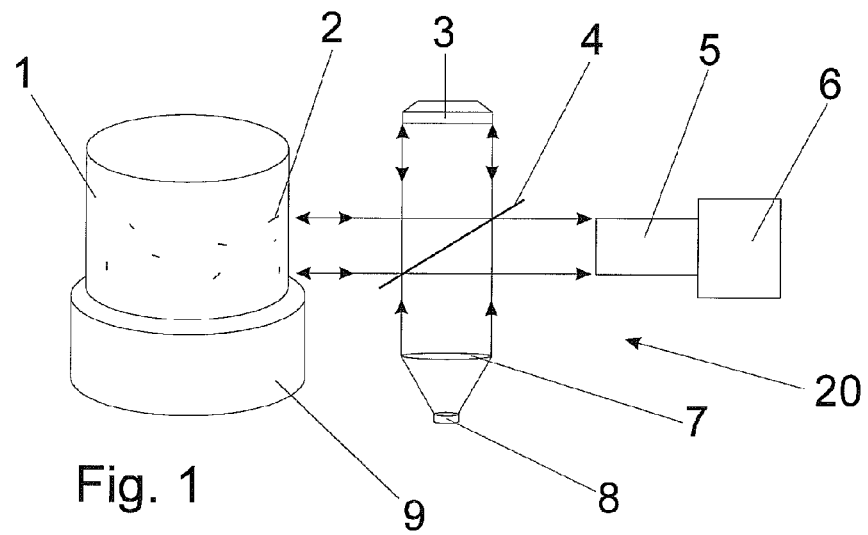
FIG. 1 is a schematic representation of a crack detection test on a component using an interferometric method.

In an embodiment, the present invention provides a method for detecting cracks in an aircraft or gas turbine component is provided in accordance with the present invention, the method encompassing at least the following method steps:

a) using an optical measurement method to determine geometric data on the component;

b) using an electronic evaluation means to analyze the geometric data, cracks and/or other damage being automatically recognized and/or classified, and the position of the cracks and/or other damage being stored.

The method makes it possible to automatically detect and identify the cracks in and/or other damage to the aircraft or gas turbine component, as well as the position of the cracks and/or other damage in relation to the component coordinate system. Depending on the findings, measures may be taken to repair the component. This eliminates the need for costly testing methods, in particular the very expensive dye penetration method. As a result, a manual component inspection is no longer required for the crack detection test, and any environmental impact is further reduced by eliminating the high energy demand required for the dye penetration method (heating of the cleaning baths and component drying) and the chemical substances (penetrant, cleaning agents and developers). Overall, therefore, the processing time needed for the particular component may be reduced and the process reliability and reproducibility enhanced.

Optical measurement methods encompass those methods which are based on visible light, infrared light, ultraviolet light or laser light. In view of the small dimensions to be determined, preference is given to those measurement methods which make use of the wave properties of light, in particular interferometric methods, coherent light being preferred. Methods based on electron beams or X-rays, ultrasound or eddy currents, for example, do not count among optical measurement methods.

The ascertained geometric data are preferably automatically compared to primarily mathematically predefined and stored nominal contours and/or tolerances and/or damage patterns. Component deviations may be classified by comparing the geometric data to predefined nominal contours and/or specific component tolerances; or damage that has occurred may be recognized through comparisons with typical damage patterns and/or comparison with the specifications of maintenance documents. It is further preferred to use background information of the componenent, for example the known component geometry, for the electronic evaluation. Together with the a matching process the electronic evaluation can automatically decide, if damages at certain component sections can geometrically occur or not. A bore hole shouldn't be classified as a damage, for instance.

The ascertained geometric data are preferably additionally utilized for measuring the component. Normally, measurements were taken following inspection of the component. This entailed outlay due to the multitude of measuring positions on the component. The accuracy of the measurement results was also largely dependent on the knowledge and thoroughness of the personnel performing the task. By utilizing the geometric data that is required anyway for the crack detection test, to measure the components, it is possible to further reduce the outlay required for component maintenance and to enhance the quality.

The method according to embodiments of the present invention is well suited for those aircraft or gas turbine components that are used as combustion chamber components of an aircraft engine. Combustion chamber components are subject to high loads, and the crack detection test normally entails a substantial outlay that may be significantly reduced by the method according to the present invention.

The geometric data are preferably ascertained using an interferometric method. In interferometry, a measurement is performed by utilizing the interference effect of light. The interferometer preferably used in carrying out the method is the Michelson interferometer, whereby coherent light is split and made to interfere with itself. By using interferometry, the cracks and/or damage may be readily detected.

The geometric data are preferably ascertained using white light interferometry. White light interferometry is preferred for detecting cracks and other damage since it permits a high-precision testing of component surfaces.

The optical measurement method is preferably carried out at a distance within the range of between 1 and 100 mm, preferably between 10 and 50 mm from the surface of the component to an optical measuring device. Previous experience has shown that good results are also obtained at the more preferred distance of 20 to 30 mm.

The analyzed geometric data are preferably used for ascertaining the requirements and/or scope of the component repair. Thus, in accordance with the test method, it is possible to directly ascertain which repairs and/or processing steps are needed to reprocess the component to the point where it meets the current requirements, for example of airworthiness certification or specifications of the aircraft engine manufacturer.

The analyzed geometric data are preferably used for a subsequent repair and/or processing of the component. The geometric data may be used in this manner for an automated welding treatment, for example. The positions of the cracks and/or of other damage in the coordinate system of the component are already known from the crack detection test, so that the repair method allows automated welding or some other type of postprocessing to be carried out at the appropriate locations. This makes it possible to eliminate additional outlay for programming and thus unwanted manual process steps in the course of a fully automated repair cycle, and for the component to be used again relatively quickly.

In an embodiment, the present invention also provides a device for detecting cracks in an aircraft or gas turbine component, the device featuring an optical measuring device and an electronic evaluation means and being equipped for implementing the described method.

Using the device, it is advantageously possible in accordance with the present invention to inspect components for cracks and other damage.

For this purpose, the device preferably includes a manipulation device for moving the measuring device and the component relative to one another. On the one hand, the component may be stationary, and the measuring device is moved toward and/or about the component, or the measuring device is fixed, and the component is moved. Finally, the component and the measuring device may also execute one movement. Thus, the manipulation device preferably includes a rotary table upon which the component is rotatable about its own axis for testing, and also a robot, whereby the measuring device is movable in an automated process into a position that is conducive to optimal results. The measuring device is preferably configured on a linear axis, realized by a linear unit or linear adjuster, for example, so as to be displaceable toward the component. Precise height images may be produced by using such a displaceably configured measuring device.

The measuring device is also well suited for detecting cracks in different-sized components since it and the component are movable relative to each other, as the optimal operating distance may be adapted to the specific component.

The measuring device is preferably moved adaptively into the best possible measuring position during the test. A path correction of the measuring device is made in response to the various component-specific geometric deviations. This path correction may be realized, for example, using a distance sensor and/or software that compares the actual geometriy with the nominel geometry during the measuring process. Preferably, the offline path correction is performed using an initial test run and/or a online path correction during the test.

The manipulation device preferably encompasses a robot arm and/or a rotary table. The measuring device or also the component may be placed in the desired position by the robot arm and/or the rotary table in an automated process.

The device preferably includes an automated stacker store in which the component and preferably also a workpiece holder are stored. The preferably modularly designed stacker store makes it possible to improve and even further automate the feeding and storing of the component. An automated transport system, which encompasses a lift unit and/or a lift station, is preferably used for transporting the component to a measurement position. Once it has been automatically selected and taken from the stacker store, for example, the component may be readily transported further via the transport system.

A workpiece holder is preferably provided for transporting and/or holding the component. The workpiece holder, preferably in conjunction with a zero-point clamping system, facilitates handling of the components in the system, and the exact positioning, efficient set up and, at the same time, rapid referencing thereof. Moreover, the workpiece holder allows automated processing of the component without the need for further reclamping in subsequent processes.

The device preferably includes a mechanism that encompasses one or a plurality of deflecting mirrors and preferably an endoscope attachment. Using these elements, the method makes it possible to access hard-to-reach component regions that otherwise would be difficult or impossible to test. Intermediate spaces of overlapping component regions or undercuts may be examined in this manner, for example. Accordingly, the device preferably includes a deflecting mirror and/or an endoscope for the measuring device.

The method is preferably carried out at a resolution within a range from 1 to 50 µm, more preferably from 5 to 30 µm, for example at approximately 10 or 20 µm. The measuring field is preferably within a range from 1 to 50 times 1 to 50 mm$^2$ (i.e., 1 to 2,500 mm$^2$), more preferably within a range from 5 to 25 times 5 to 25 mm$^2$ (i.e., 25 to 625 mm$^2$), for example approximately 20 times 20 mm$^2$ (i.e., 400 mm$^2$) It can also be advantageous for the measuring field to be within a range from 0.25 to 50 times 0.25 to 50 mm$^2$ (i.e., 0.0625 to 2,500 mm$^2$), more preferably within a range from 1 to 15 times 1 to 15 mm$^2$ (i.e., 1 to 225 mm$^2$), for example approximately 3 times 3 mm$^2$ (i.e., 9 mm$^2$)

FIG. 1 shows an aircraft or gas turbine component 1 that is mounted on a workpiece holder 9. Component 1 may be a CFR component, for example a structural component, or a metallic component, for example a landing-gear component. Moreover, component 1 may also come from a stationary gas turbine. It is a component 1 that was once in use in an aircraft and is now examined being disassembled from the rest of the aircraft. In this exemplary embodiment, component 1 is from the combustion chamber of an aircraft engine. The surface of the combustion chamber component is to be inspected for the existence of possible defects, for example cracks 2, burns, deformations or other damage. Such a test is normally carried out in the course of engine component maintenance after the component 1 has been cleaned. Standards and requirements for component quality exist that are stipulated by aviation regulations. Thus, cracks 2 in combustion chamber components are only permissible to a certain extent. Also, the permissible crack geometry, for example the maximally allowable size of cracks 2, is prescribed. To meet these requirements, a crack detection test is normally performed using the dye penetration method mentioned at the outset. However, the described disadvantages are associated with the method.

To obviate the necessity of the costly dye penetration method, an optical measuring method, preferably an interferometric method is used in accordance with the present invention to detect the cracks in the combustion chamber component. White light interferometry is preferably used. As illustrated in FIG. 1, a measuring device 20, in particular an interferometer, is provided for this purpose. Measuring device 20 includes a coherent light source 8, in particular a laser having a collimator 7, for supplying parallel coherent light. Moreover, measuring device 20 includes a beam splitter 4, a reference mirror 3, as well as a camera unit 6 having an objective unit 5.

The combustion chamber component to be inspected and reference mirror 3 are simultaneously illuminated by the coherent broadband light from light source 8. To this end, the light waves in beam splitter 4 are split into two light packets. The combustion chamber component and reference mirror 3 reflect the light waves which, in turn, strike camera unit 6 via beam splitter 4. Interference patterns are then formed when the wavelength to component 1 conforms with that to reference mirror 3. This interference pattern or variations in brightness is/are detected by camera unit 6. Maximum constructive interference occurs when superposition takes place in phase and in order. If the wave packets converge in phase, but displaced in order and partially overlapping, a less pronounced constructive interference is obtained. If the wave packets strike the detector in succession, then no interference is produced.

The software analyzes the measured variations in brightness. An evaluation means 14 used for the analysis may encompass camera unit 6 and/or one or a plurality of computers. Using mathematical algorithms which assign height values to the variations in brightness, geometric data are ascertained or generated by the measurements. A height value is mathematically assigned to each pixel, thereby generating what is generally referred to as a "point cloud." This makes it possible to determine the topography of the component surface at a resolution that is within the range of the surface roughness. The component surface may be examined for damage at a resolution of 0.3 µm to 130 µm and a measuring field of 0.3 times 0.3 mm$^2$ to 130 times 130 mm$^2$ (i.e., 0.09 to 16,900 mm$^2$); the examination is preferably performed at a resolution within a range from 1 to 50 µm, more preferably from 5 to 30 µm, for example at approximately 10 or 20 µm. The measuring field is preferably within a range from 1 to 50 times 1 to 50 mm$^2$ (i.e., 1 to 2,500 mm$^2$), more preferably within a range from 5 to 25 times 5 to 25mm$^2$ (i.e., 25 to 625mm$^2$), for example approximately 20 times 20 mm$^2$ (i.e., 400 mm$^2$) It can also be advantageous for the measuring field to be within a range from 0.25 to 50 times 0.25 to 50 mm$^2$ (i.e., 0.0625 to 2,500 mm$^2$), more preferably within a range from 1 to 15 times 1 to 15 mm$^2$ (i.e., 1 to 225 mm$^2$), for example approximately 3 times 3 mm$^2$ (i.e., 9 mm$^2$) Cracks 2 and/or other, to some extent, very minimal damage may be detected and identified.

The ascertained geometric data are preferably compared to storable nominal contours and/or tolerances and/or typical damage patterns in an automated process. These nominal contours and/or tolerances and/or typical damage patterns may be earlier geometric data, for example, that originated from same component 1 and that had been stored during the most recent maintenance and crack inspection test. The tolerances may be obtained from the specifications stipulated by aviation regulations, for example, whereby, following the method according to the present invention, the information as to whether component 1 meets the specifications or whether repairs are still needed, is directly available. Repairs may encompass the sealing of cracks 2 in welding operations, for example. The aim is to restore component 1 in such a way that it meets the safety requirements and is thus airworthy again.

In the course of the test procedure, the measurement data are preferably analyzed in a linked computer cluster that is preferably included in evaluation means 14 as well. The measured component surface is preferably first converted to a plane using mathematical transformations, and the surface curvature is computed therefrom. The computer, respectively the software used, is preferably set up to assign specific features or combinations of features or surface properties, which meet certain predefined conditions, for example the property "crack" or "damage," and to store the coordinates of these findings. The findings, also referred to as damage patterns, may be thereby displayed on a computer screen, for example, the information on the position—thus the absolute position in the coordinate system used—being stored. Component 1 may be preferably displayed, together with the findings, on a computer screen, "critical" findings, thus those that require a postprocessing, being specially identified. The ascertained geometric data are additionally utilized for measuring component 1. Under the current state of the art, these measurements are normally taken manually following the crack detection test and represent a separate, time-consuming operation. In contrast, the method according to the present invention eliminates the need for additional geometric measurements, respectively for an additional operation.

The ascertained geometric data and the findings, such as cracks 2, burns or other damage, are preferably stored in the form of polylines and/or polygons. The geometric data, which, as described, initially exist in the form of a point cloud, are transformed by what is generally referred to as a "meshing" or "paving" process and by surface feedback into a CAD model. This model may be utilized for other automated, preferably adaptively automated processing steps.

The relevant component dimensions may be recorded as well already in the course of the crack detection test. Component dimensions, which are to be documented in accordance with the maintenance and service regulations, are automatically stored and are preferably also available as a log. The dimensions are preferably determined at predefined measuring positions, making it possible to thereby achieve a high reproducibility and process reliability of the measuring process. The measurement data are subsequently transmitted to one or a plurality of linked computers. The computer(s) is/are configured to analyze the measurement data. The measurement data are preferably stored in a database in order to permit a long-term documentation. This makes it possible to observe the change in same component 1 over its lifetime. Over the lifetime thereof, components 1 normally pass several times through the maintenance and service processes, and the ascertained data may then be compared to the data of the preceding maintenance and service.

The computer, respectively the computer unit used is preferably capable of transmitting the collected measurement values directly via a data interface into the electronic documentation system of the appropriately assigned workshop. Any deviation from the nominal contour of component 1, respectively deviations which exceed permissible tolerances may preferably be optically represented for the technical personnel on what is generally referred to as the "user interface." This allows the technical personnel to quickly and accurately assess in terms of measurement, how to proceed with the maintenance and servicing of component 1.

Figure 2:
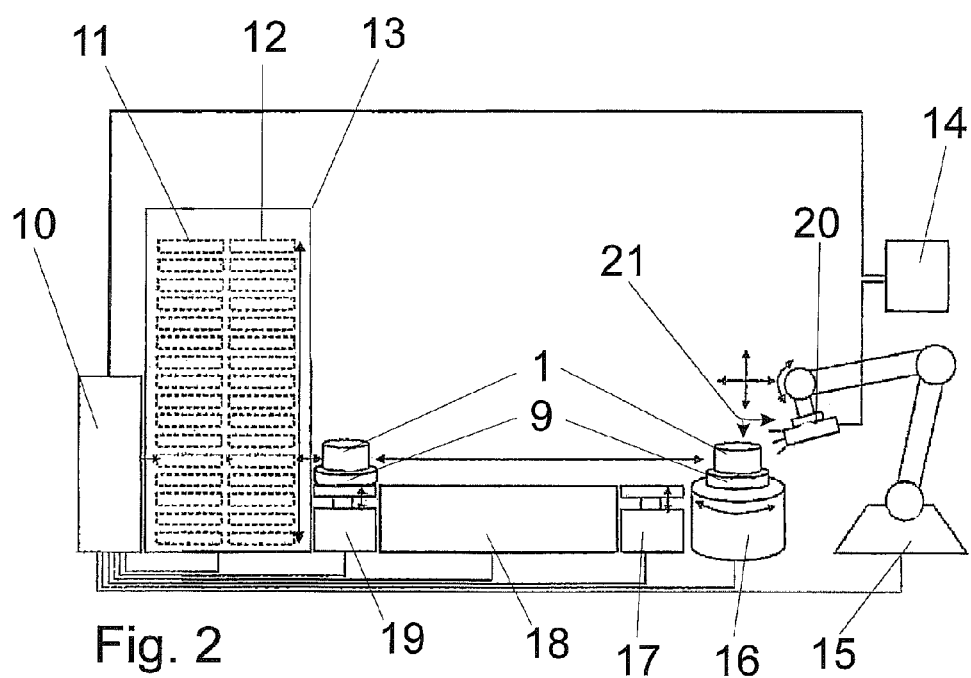
FIG. 2 is a representation of a method according to an embodiment of the present invention for detecting cracks, as well as of a device according to an embodiment of the present invention for implementing the method.

The entire component inspection preferably takes place in a fully automated process. FIG. 2 illustrates a fully automated component inspection of this kind that encompasses a crack detection test and measurement of the components. The process of establishing the scope of the repair (for example, "crack with weld seam" or "crack cluster with patch") is likewise carried out in an automated fashion. A "crack cluster" denotes a special crack structure where a plurality of cracks are interconnected at least one location or lie densely together. In the case of a "crack cluster with patch" repair, the defective region is separated from component 1, and a replacement part, the "patch," also referred to as "repair patch," is used in place thereof and is joined to component 1 to be repaired. The replacement part preferably originates from another component which, as a whole, is no longer airworthy, but, at least, whose removed replacement part portion still meets the requirements stipulated by aviation regulations.

As described, detected damage is classified by predefined damage characteristics and/or tolerances and/or damage patterns, flagged in the collected measurement data and, on the basis thereof, an appropriate processing strategy (for example, a welding treatment) may be established. A fully automated processing may be provided in which component 1 is automatically repaired at the defective locations, or a partially automated processing may be provided, whereby, in accordance with the method, for example, only the process of marking the locations to be repaired using an identification means is automated, however, further repair steps (such as welding operations, for example) are still performed manually.

Component 1 to be tested is initially located in component holding magazine 12 along with other components 1 to be tested. Component holding magazine 12 is a part of automated stacker store 13. Besides component holder magazine 12, automated stacker store 13 additionally includes a workpiece holder magazine 11. Workpiece holders 9 are stored in workpiece holder magazine 11. Individual workpiece holders 9 may be suited for individual or a plurality of types of components 1.

Located downstream of stacker store 13 is an automated transport system 18. This includes a lift station 19 at stacker store 13, as well as a lift unit 17 at rotary table 16. Rotary table 16 is part of a manipulation device 21, which also encompasses a robot arm 15. Robot arm 15 is able to place measuring device 20, which corresponds to measuring device 20 of FIG. 1, and component 1 in the desired position, respectively measuring position, in an automated process.

An evaluations means 14, which is used in the manner already described for analyzing the geometric data ascertained by the optical measurement method, is linked to measuring device 20.

A control device 10 and/or a regulating device is also provided that is configured to control and/or regulate the functional sequence of the process and/or to allow it to proceed automatically. Regulating or control device 10 is preferably able to perform an in-process closed-loop control. The regulating or control device 10 is alternatively able to perform an online and/or offline control of the measurement process.

The combustion chamber component is stored in automated stacker store 13. Information on task prioritization and selection of the test method, respectively of the test program and or workpiece holder 9, is preferably communicated to control device 10 by the reading-in of a bar code or a data matrix code.

If the combustion chamber component is to be tested fully automatically, a series of automated steps take place. A workpiece holder 9 suited for the combustion chamber component is first selected from the system and placed on lift station 19. Following the subsequent lowering of lift station 19, the combustion chamber component is transferred from storage to workpiece holder 9. A mechanical interface between workpiece holder 9 and lift station 19 preferably activates the fastening (for example, clamping) of component 1 in workpiece holder 9. Workpiece holder 9, together with component 1, is moved by transport system 18 to lift unit 17 and transported via the same to rotary table 16. If necessary, the component 1 can also manually placed on the rotary table 16 and the test method and the test program can also be manually chosen at the control device 10.

Upon transmission of a signal indicative thereof to control device 10 via an interface between workpiece holder 9 and rotary table 16, the process of ascertaining the geometric data begins. Robot arm 15 advances measuring device 20 toward the component surface by a defined distance of preferably 20 to 30 mm. To this end, the robot arm preferably has a linear unit or linear adjuster. Manipulation device 21 moves measuring device 20 and component 1 to the desired measuring positions. Certain preferred measuring methods, respectively measuring programs, which constitute part of the testing method, respectively testing program, and are suited for component 1 and other aircraft or gas turbine components 1, may be specified for control device 10. which measuring method is to be carried out using which measuring positions for which component 1 preferably stored in control device 10. The distance sensor, which is part of the measuring device 20, determines geometry data on the component 1, which are used for calibrating the actual geometry with the nominal geometry of the component 1. Based on this data a path correction of the manipulating device 21 can be performed. Rotary table 16 preferably moves component 1 past measuring device 20 in a clocked operation. It is also preferable that rotary table 16 moves component 1 past measuring device 20 in a continuously rotating process. In the case of a clocked rotation, the clocked interval preferably corresponds to an image width considered circumferentially, the images preferably overlapping to permit complete acquisition of the component surface. The individual images preferably overlap by 0.1 to 10 mm, preferably by 0.5 to 5 mm, and more preferably by 1 to 2 mm. The individual images can preferably also overlap by 0.01 to 5 mm, preferably by 0.05 to 3 mm, and more preferably by 0.1 to 1 mm. The associated evaluation means 14 analyzes the images, respectively geometric data. Cracks 2 having a crack width of at least 5 µm, more preferably of at least 20 µm, are preferably detected. Cracks 2 having a crack width of at least 1 µm, more preferably of at least 10 µm, are preferably also detected. Damage is also identified and classified by evaluation means 14. The results of these findings may be indicated and examined as needed on a computer screen, for example. On the basis of the results, the responsible technical personnel decides whether and, in some instances, which further maintenance and servicing measures are required. This is accomplished via a man-machine interface, what is generally referred to as a "user interface." Preferably, on the basis of the findings, what is generally referred to as an "expert system" using predetermined characteristics and/or tolerances and/or rules and/or typical damage patterns and/or former decisions independently decides by an in-process closed-loop control, within an automated repair process chain, which further maintenance and servicing measures are necessary and introduces them accordingly.

Therefore, the device for detecting cracks in an aicraft engine preferably comprises evaluation means 14 that automatically evaluate the geometric data for identification and/or classification of the damages using predefined component 1 characteristics and/or nominal contours and/or tolerances and/or damage patterns and/or learned rules and/or previous knowledge of the expected geometric data. Furhtermore it preferably comprises a optical measuring device 20 that uses a distance sensor, which, using a control device 10, allows an automatic online and/or offline adaptive path correction of the manipulation device 21.

While the invention has been particularly shown and described with reference to preferred embodiments thereof, it will be understood by those skilled in the art that various changes in form and details may be made therein without departing from the spirit and scope of the invention.

LIST OF REFERENCE NUMERALS

1 component
2 crack
3 reference mirror
4 beam splitter
5 objective unit
6 camera unit
7 collimator
8 light source
9 workpiece holder
10 control device
11 workpiece holder magazine
12 component holder magazine
13 stacker store
14 evaluation means
15 robot arm
16 rotary table
17 lift unit
18 transport system
19 lift station
20 measuring device
21 manipulation device

What is claimed is:

1. A method for detecting cracks in an aircraft or gas turbine component, the method comprising:
    ascertaining geometric data about the component using an optical measurement method, the optical measurement method being carried out at a distance from a surface of the component being measured using a distance sensor configured to measure the distance between a measurement device and the surface of the component, and using a white light interferometer having a beam splitter;

analyzing the geometric data, using an electronic evaluation device, so as to at least one of recognize and classify, automatically, at least one of cracks and other damage; and storing a position of the at least one of cracks and other damage.

2. The method recited in claim 1, wherein the ascertained geometric data are automatically compared to mathematically predefined and stored data relating to at least one of nominal characteristics, contours, tolerances and damage patterns.

3. The method recited in claim 1, wherein the ascertained geometric data are used for measuring the component.

4. The method recited in claim 1, wherein the component is a combustion chamber component of an aircraft engine.

5. The method recited in claim 1, further comprising ascertaining at least one of requirements and scope of repair of the component using the analyzed geometric data.

6. The method recited in claim 5, further comprising at least one of repairing and processing the component using the analyzed geometric data.

7. The method recited in claim 6, wherein the at least one of repairing and processing is automated.

8. The method recited in claim 1, further comprising measuring variations in brightness and assigning height values to each pixel of the geometric data.

9. The method recited in claim 8, further comprising generating a computer model of the component by meshing or paving the height values, wherein the at least one of cracks and other damage are represented as at least one of polylines and polygons in the model.

10. The method as recited in claim 1, further comprising comparing the ascertained geometric data to mathematically predefined and stored data relating to damage patterns so as to determine a scope of repair, and then repairing the component based on the determined scope of repair.

* * * * *